(12) United States Patent
Mizukami et al.

(10) Patent No.: US 8,491,887 B2
(45) Date of Patent: Jul. 23, 2013

(54) ANTICANCER THERAPY BY TRANSPLANTING VASCULAR ENDOTHELIAL PROGENITOR CELLS

(75) Inventors: Yusuke Mizukami, Hokkaido (JP); Yutaka Kohgo, Hokkaido (JP); Kazumasa Nakamura, Hokkaido (JP)

(73) Assignee: National University Corporation Asahikawa Medical University, Hokkaido (JP)

( * ) Notice: Subject to any disclaimer, the term of this patent is extended or adjusted under 35 U.S.C. 154(b) by 494 days.

(21) Appl. No.: 12/600,530

(22) PCT Filed: May 19, 2008

(86) PCT No.: PCT/JP2008/001247
§ 371 (c)(1),
(2), (4) Date: Feb. 1, 2010

(87) PCT Pub. No.: WO2008/142862
PCT Pub. Date: Nov. 27, 2008

(65) Prior Publication Data
US 2010/0143311 A1  Jun. 10, 2010

(30) Foreign Application Priority Data
May 18, 2007  (JP) ................. 2007-133486

(51) Int. Cl.
*A61K 35/12* (2006.01)
(52) U.S. Cl.
USPC ........................................ 424/93.7
(58) Field of Classification Search
None
See application file for complete search history.

(56) References Cited

U.S. PATENT DOCUMENTS 5,980,887 A * 11/1999 Isner et al. .................... 424/93.7
2007/0082397 A1* 4/2007 Hasson et al. ................ 435/366

FOREIGN PATENT DOCUMENTS

| JP | 2001-231549 A | | 8/2001 |
| JP | 2003-250820 A | | 9/2003 |
| JP | 2007-089536 A | | 4/2007 |
| WO | WO2006010558 | * | 2/2006 |

OTHER PUBLICATIONS

Wei et al., Embryonic endothelial progenitor cells armed with a suicide gene target hypoxic lung metastases after intravenous delivery, 2004, Cancer Cell 5: 477-488.*
Hylander et al., The anti-tumor effect of Apo2L/TRAIL on patient pancreatic adenocarcinomas grown as xenografts in SCID mice, 2005, Journal of Translational Medicine 3: 22, pp. 1-13.*
Hilbe et al., CD133 positive endothelial progenitor cells contribute to the tumour vasculature in non-small cell lung cancer, 2004, Journal of Clinical Pathology 57: 965-969.*
Acker, T. et al. Role of hypoxia in tumor angiogenesis—molecular and cellular angiogenic crosstalk. In: Cell Tissue Research; 2003; vol. 314; pp. 145-155.
Office action in counterpart European patent application No. EP 08751765.2; issued Jul. 8, 2011.
Keith, Brian et al; Hypoxia-Inducible Factors, Stem Cells, and Cancer. In: Cell; vol. 129, No. 3; May 2007; pp. 465-472. (XP-002613546).
Sasajima, Junpei et al; Transplanting Normal Vascular Proangiogenic Cells to Tumor-Bearing Mice Triggers Vascular Remodeling and Reduces Hypoxia in Tumors. In: American Association for Cancer Research; vol. 70, No. 15; Aug. 1, 2010; pp. 6283-6292. (XP-002613547).
European Search Report for counterpart application No. EP08751765; Dec. 9, 2010.
Asahara et al; "Vascular regeneration therapy using endothelial progenitor cells", Experimental Medicine, vol. 24, No. 1 pp. 30-36, 2006.
Ii et al; "Discovery of endothelial progenitor cells and the perspective for therapeutic application", Experimental Medicine, vol. 24, No. 18, pp. 2871-2879, 2006.
Asahara et al; "Isolation of Putative Progenitor Endothelial Cells for Angiogenesis", Science Magazine, vol. 275, pp. 964-967, 1997.
Assmus; Transplantation of Progenitor Cells and Regeneration Enhancement in Acute Myocardial Infarction (TOPCARE-AMI), Clinical Investigation and Reports, pp. 3009-3017, 2002.
Ii et al; "Endothelial Progenitor Thrombospondin-1 Mediates Diabetes-Induced Delay in Reendothelialization Following Arterial Injury", Circulation Research, pp. 697-704, 2006.
Muta et al; "Study of cancer gene therapy using IL-12-secreting endothelial progenitor cells in a rat solid tumor model", Oncology Reports, pp. 1765-1769, 2003.
Oh et al; "Tumor Angiogenesis Promoted by Ex vivo Differentiated Endothelial Progenitor Cells Is Effectively Inhibited by an Angiogenesis Inhibitor, TK1-2", Cancer Research, pp. 4851-4859, 2007.
Kalka et al, "Endothelial progenitor cells: from bench to bedside", Future Cardiology 2006, vol. 2, No. 4, pp. 455-466.
Yasufumi Sato "Persistent vascular normalization as an alternative goal of anti-angiogenic cancer therapy" Cancer Sci, Jul. 2011, pp. 1253-1256, vol. 102 No. 7, Japanese Cancer Association.
Shom Goel et al "Normalization of the Vasculature for Treatment of Cancer and Other Diseases" Physiol Rev, Jul. 2011, vol. 91, pp. 1071-1121.
Junpei Sasajima et al "Transplanting Normal Vascular Proangiogenic Cells to Tumor-Bearing Mice Triggers Vascular Remodeling and Reduces Hypoxia in Tumors," Cancer Research, Aug. 1, 2010, pp. 6283-6292, vol. 70 No. 15.

* cited by examiner

*Primary Examiner* — Jon P Weber
*Assistant Examiner* — Robert Yamasaki
(74) *Attorney, Agent, or Firm* — Pearne & Gordon LLP

(57) ABSTRACT

An anticancer therapy using autologous cells or the like, which induces the regression of cancer or has favorable drug delivery effects and brings about reduction or withdrawal of a hypoxic region(s) in tumor is provided. Transplantation of endothelial progenitor cells, via intravenously or other methods leads to tumor growth inhibition, an increase of the vascular density with an enlargement of the vascular diameter, and reduction of a hypoxic region(s) in the tumor. Allogeneic transplantation of endothelial progenitor cells may be achieved to secure the cells for the therapy, however, autologous transplantation of endothelial progenitor cells from cancer patients would be desirable to evade rejection. When autologous cells are used, mononuclear cells are separated from the peripheral blood or bone marrow of the patient and cultured using an endothelial differentiation medium containing cytokines such as VEGF to obtain adherent cells, which can then be collected and used as endothelial progenitor cells.

10 Claims, 6 Drawing Sheets

CONTROL (PBS)  EPC TRANSPLANTATION ($10^5$)

CONTROL (PBS)  EPC TRANSPLANTATION ($10^5$)

ANTICANCER THERAPY BY TRANSPLANTING VASCULAR ENDOTHELIAL PROGENITOR CELLS

TECHNICAL FIELD

The present invention relates to: a preventive or therapeutic preparation for tumor comprising cells including endothelial progenitor cells (EPC) obtained by inducing the differentiation of peripheral blood or bone marrow mononuclear cells; a method for tumor prevention or treatment comprising transvenously administering an endothelial progenitor cell; use of endothelial progenitor cells in the production of a drug for tumor prevention or treatment, etc.

BACKGROUND ART

Examples of conventional methods for tumor (cancer) treatment include treatment methods using chemical anticancer agents or radiation. However, the cancer treatment using anticancer agents, radiation, or the like dose not produce sufficient therapeutic effects. One reason therefor may be that cancer tissues are placed in a hypoxic environment. Although attempts such as hyperthermia and hyperbaric oxygenation have been made as methods for controlling this hypoxic environment, sufficient therapeutic effects have not been established yet. Moreover, reduction in drug activity caused by inappropriate drug distribution is responsible for the mechanism underlying resistance to anticancer agents. In this event, the structural or functional abnormality of tumor vessels is probably involved. To solve these problems, treatment based on immunotherapy in combination with a drug delivery system using nanoparticles, micelle, or the like has been practiced as a conventional technique.

On the other hand, endothelial progenitor cells obtained from bone marrow or the like are cells responsible for revascularization (see e.g., Non-Patent Document 1). For revascularization therapy, autologous endothelial progenitor cells are transplanted to patients with ischemic heart disease or arterial occlusive disease (see e.g., Non-Patent Documents 2 to 4). The endothelial progenitor cells can be separated and collected from bone marrow as well as from peripheral blood, cord blood, or the like. These cells are characterized by having surface markers, for example, CD34 or VEGFR2 (FLK-1), and can be separated from mononuclear cells using magnetic beads or flow cytometry. Likewise, these cells can also be collected as adherent cells obtained by culturing mononuclear cells using an endothelial differentiation medium containing cytokines such as VEGF. These adherent cells are characterized by having uptake of acetylated low-density lipoprotein (acetylated LDL) and being capable of binding to lectin. CD34-positive mononuclear cells obtained from bone marrow are mainly used in the revascularization therapy currently performed using the endothelial progenitor cells.

Animal experiments related to cancer treatment strategy have been reported, in which mouse endothelial progenitor cells obtained from bone marrow or the like, or rat-derived endothelial progenitor cell-like cells are genetically modified and used as carriers (see e.g., Non-Patent Document 5). However, the document discloses that tumor growth was observed in cancer-bearing animals having the transplanted rat-derived endothelial progenitor cell-like cells (immortalized cells). Thus, the use of such immortalized cells in cancer treatment raises serious concerns.

Other methods have been reported, including: a method for preparing mouse endothelial progenitor cells as adherent cells from mouse bone marrow cells (see e.g., Non-Patent Document 6); a method comprising: preparing endothelial progenitor cells from a mononuclear cell fraction collected from the bone marrow of transgenic mice carrying an introduced large T-antigen gene of a temperature-sensitive mutant tsA58 of SV40; subsequently differentiating these endothelial progenitor cells into endothelial cells by culture; and subculturing the differentiated endothelial cells to establish an immortalized endothelial cell strain which has acetylated LDL uptake activities and expresses VEGF (vascular endothelial growth factor) receptor 1, TIE1, and TIE2 (see e.g., Patent Document 1); a method comprising coculturing, in a contact state, undifferentiated bone marrow cells and cells highly expressing Notch ligands such as Jagged-1 or Delta-4 to induce the differentiation of the undifferentiated bone marrow cells into endothelial progenitor cell-like cells (see e.g., Patent Document 2); and a revascularization method comprising: passing a cell suspension containing endothelial progenitor cells and contaminating cells, through a cell separation filter that substantially permits passage of at least the contaminating cells therethrough and substantially captures the endothelial progenitor cells; introducing a fluid into the cell separation filter to collect the endothelial progenitor cells captured by the cell separation filter; and using the collected endothelial progenitor cells in revascularization (Patent Document 3).

Patent Document 1: Japanese Patent Laid-Open No. 2001-231549
Patent Document 2: Japanese Patent Laid-Open No. 2007-89536
Patent Document 3: Japanese Patent Laid-Open No. 2003-250820
Non-Patent Document 1: Asahara T, et al: Science 275; 964-967, 1997
Non-Patent Document 2: Assmus B, et al: Circulation 106; 3009-3017, 2002
Non-Patent Document 3: Asahara T, et al: Experimental Medicine, vol. 24, No. 1, p. 30-36, 2006
Non-Patent Document 4: Ii M, et al: Experimental Medicine, vol. 24, No. 18, p. 2871-2879, 2006
Non-Patent Document 5: Muta M, et al: Oncology Report 10; 1765-1769, 2003
Non-Patent Document 6: Ii M, et al: Circulation Research 98; 697-704, 2006

DISCLOSURE OF THE INVENTION

Problems to be Solved by the Invention

An object of the present invention is to provide anticancer therapy using autologous cells or the like, which induces the regression of cancer or has favorable drug delivery effects and brings about reduction or withdrawal of a hypoxic region(s) in tumor.

Means for Solving the Problems

If the structural modification (remodeling) of tumor vessels can be induced for tumor in which drug distribution is poor, it is expected that the hypoxic environment of the tumor is withdrawn and further, the drug distribution is improved. Thus, the present inventors focused on the revascularization ability of endothelial progenitor cells. However, the present inventors could not predict the influence of transplantation of the endothelial progenitor cells having the revascularization ability on tumor, because angiogenesis inhibitors are well known to have growth inhibitory activity against malignant tumor and inhibitory activity against invasion and metastasis.

However, the present inventors conducted an experiment of transplanting mouse endothelial progenitor cells to cancer-bearing mice (of the same species as the endothelial progenitor cells) prepared by the hypodermic transplantation of human pancreatic cancer cells, and consequently revealed, first of all, that the transplantation of the endothelial progenitor cells inhibits tumor growth. It was found that the transplantation of the endothelial progenitor cells, which are responsible for revascularization (vascular formation), significantly changes tumor vessel construction, though the detailed mechanism thereof remains to be elucidated. Specifically, the tumor prepared by the hypodermic transplantation of human pancreatic cancer cells is characterized by hypovascularity as seen in the human pancreatic cancer tissues. The transplantation of the endothelial progenitor cells was observed to increase the vascular density and enlarge the vascular diameter. This phenomenon can also be regarded as maturation of immature tumor vessels. Reduction of the hypoxic region(s) in the tumor was confirmed as a phenomenon consistent with an expected increase of blood flow.

Specifically, the present invention relates to: a preventive or therapeutic preparation for tumor, characterized by comprising endothelial progenitor cells; a preparation for inhibiting tumor growth, characterized by comprising endothelial progenitor cells; a preparation for reducing a hypoxic region(s) in tumor, characterized by comprising endothelial progenitor cells; a preparation for inducing remodeling of tumor vessels, characterized by comprising endothelial progenitor cells; a preparation for enhancing activity of anticancer agents, characterized by comprising endothelial progenitor cells; and a preparation for enhancing effect of radiotherapy, characterized by comprising endothelial progenitor cells.

Moreover, the present invention relates to: a method for tumor prevention or treatment, characterized by comprising transvenously administering endothelial progenitor cells to a mammal; a method for inhibiting tumor growth, characterized by comprising transvenously administering endothelial progenitor cells to a mammal; a method for reducing a hypoxic region(s) in tumor, characterized by comprising transvenously administering endothelial progenitor cells to a mammal; and a method for inducing remodeling of tumor vessels, characterized by comprising transvenously administering endothelial progenitor cells to a mammal.

Furthermore, the present invention relates to: use of endothelial progenitor cells in the production of a drug for tumor prevention or treatment; use of endothelial progenitor cells in the production of a drug for tumor growth inhibition; use of endothelial progenitor cells in the production of a drug for reduction of a hypoxic region(s) in tumor; and use of endothelial progenitor cells in the production of a drug for induction of remodeling of tumor vessels.

BEST MODE FOR CARRYING OUT THE INVENTION

Figure 1:
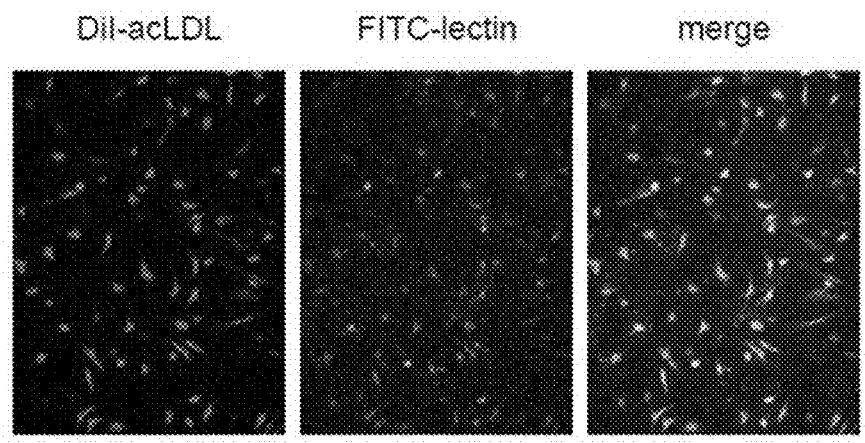
FIG. 1 is a diagram showing that endothelial progenitor cells separated and prepared from bone marrow exhibit uptake of acetylated LDL and affinity for FITC-lectin.

A preventive or therapeutic preparation for tumor, a preparation for inhibiting tumor growth, a preparation for reducing a hypoxic region(s) in tumor, a remodeling inducer for tumor vessels, a preparation for enhancing activity of anticancer agents, and a preparation for enhancing effect of radiotherapy according to the present invention are not particularly as long as these preparations are compositions comprising endothelial progenitor cells as an active ingredient. Moreover, a method for tumor prevention or treatment, a method for inhibiting tumor growth, a method for reducing a hypoxic region(s) in tumor, and a method for inducing remodeling of tumor vessels according to the present invention are not particularly limited as long as these methods comprise transvenously administering endothelial progenitor cells to a mammal of the same species as the collected endothelial progenitor cells. Furthermore, use (method) according to the present invention is not particularly limited as long as this use is use of endothelial progenitor cells in the production of any of a drug for tumor prevention or treatment, a drug for tumor growth inhibition, a drug for reduction of a hypoxic region(s) in tumor, and a drug for induction of remodeling of tumor vessels. The tumor means solid cancer. The solid cancer can be exemplified specifically by pancreatic cancer, esophagus cancer, gastric cancer, lung cancer, kidney cancer, thyroid cancer, parotid cancer, head and neck cancer, bone and soft tissue sarcoma, ureter cancer, bladder cancer, uterine cancer, liver cancer, breast cancer, ovarian cancer, and uterine tube cancer and can be exemplified particularly preferably by hypovascular cancer such as pancreatic cancer.

The preventive or therapeutic preparation for tumor according to the present invention can prevent or treat tumor, through the following mechanism, by transvenously administering a mammal (e.g., human, mouse, rat, dog, cow, or monkey)-derived, particularly, human-derived endothelial progenitor cells to a mammal of the same species as the endothelial progenitor cells, particularly, a human: the administered endothelial progenitor cells move to the tumor tissue such that the cells are incorporated in the tumor tissue, in which the endothelial progenitor cells in turn bring about structural or functional change such as enlargement of tumor vessel caliber and improvement of blood flow to induce the correction of the abnormality, reduce a hypoxic region(s) in the tumor, and inhibit tumor growth. The preparation for inhibiting tumor growth according to the present invention can inhibit tumor growth by transvenously administering endothelial progenitor cells. The preparation for reducing a hypoxic region(s) in tumor according to the present invention can reduce a hypoxic region(s) in tumor by transvenously administering endothelial progenitor cells. The remodeling inducer for tumor vessels according to the present invention can induce remodeling (structural modification) of tumor vessels, such as enlargement of tumor vessel caliber and improvement of blood flow, by transvenously administering endothelial progenitor cells. The preparation for enhancing activity of anticancer agents according to the present invention can increase blood flow in tumor, improve the distributed state of anticancer preparations in the tumor tissue, and enhance the activity of the anticancer agents, by transvenously administering endothelial progenitor cells. The preparation for enhancing effect of radiotherapy according to the present invention can enhance the therapeutic effect of radiation by transvenously administering endothelial progenitor cells.

In the present invention, the endothelial progenitor cell(s) means an adherent cell(s) that is present in blood such as mammalian peripheral blood, bone marrow, and cord blood and has the property of proliferating through adherence to extracellular matrix. Examples thereof can preferably include: cells having the ability to differentiate into endothelial cells; and a heterogenous cell population (group) that does not directly differentiate into endothelial cells but promotes the construction and formation of neovascular vessels via, for example, the production of various cytokines. The extracellular matrix is not particularly limited as long as the extracellular matrix is a matrix, substrate, or carrier on which cells are capable of dividing and proliferating through adherence thereto in cell culture. Examples thereof can include extracellularly existing structures that play a role as anchorages in cell adhesion or play a role in retaining or providing growth factors or the like, and can specifically include fibronectin, vitronectin, collagen, proteoglycan, laminin, tenascin, entactin, elastin, fibrillin, hyaluronic acid, gelatin, poly-L-lysine, and poly-D-lysine. Examples of a production method for the endothelial progenitor cells can include a method comprising culturing mononuclear cells separated from peripheral blood or bone marrow according to a standard method, using an endothelial differentiation promotion medium containing cytokines such as VEGF, and collecting adherent cells obtained by the culture. Moreover, of endothelial progenitor cells, cells expressing surface markers such as CD34 or VEGF receptor 2 can be separated from mononuclear cells by a method using magnetic beads bound with antibodies binding to these surface markers or by flow cytometry using fluorescently labeled antibodies.

Examples of the endothelial progenitor cells can specifically include: cells having acetylated LDL uptake activities and/or lectin affinity; cells expressing CD34 and/or a VEGF receptor; cells expressing CD105 and/or CD31; cells expressing c-Kit and/or VEGF receptor 2 (Flk-1); cells expressing VE-cadherin; cells expressing CD11b; cells expressing CD105; and/or cells expressing Tie2 (CD202); and cells having the properties of these cells in combination.

Moreover, cancer patient-derived autologous cells are more preferably used, because rejection that may be caused by the transvenous administration of the endothelial progenitor cells can be suppressed. When the autologous cells are used, mononuclear cells are separated from the peripheral blood or bone marrow of the patient and cultured using an endothelial differentiation promotion medium containing cytokines such as VEGF to obtain adherent cells, which can then be collected and advantageously used as endothelial progenitor cells. Furthermore, endothelial progenitor cells that are not subjected to genetic engineering such as immortalization is preferably used in terms of safety secured in cell therapy, because tumor growth as seen in the transplantation of rat-derived endothelial progenitor cell-like cells can be prevented. In this context, there may be the possibility of promoting tumor growth or metastasis after long-term observation, due to the hyperplasia of a mature tumor vessel of the transplanted endothelial progenitor cells. As measures against such a harmful event attributed to the endothelial progenitor cell transplantation, the endothelial progenitor cells are subjected in advance to gene transfer with suicide genes such as thymidine kinase genes. If necessary, cancer tissues together with the tumor vessel may be destroyed by the administration of ganciclovir or the like.

When the drug for tumor prevention or treatment (preventive or therapeutic preparation for tumor), preferably a drug to be transvenously administered, is produced, various formulated ingredients for preparations can be added thereto, such as pharmaceutically acceptable, usual carriers, excipients, diluents, pH buffers, water-soluble solvents (e.g., saline), tonicity agents (e.g., sodium chloride, glycerin, and D-mannitol), stabilizers (e.g., human serum albumin), preservatives (e.g., methylparaben), and local anesthetics (e.g., benzyl alcohol). Moreover, this drug can also be used in combination with an additional antitumor agent. The dose of the endothelial progenitor cells transvenously administered can be, for example, $1 \times 10^5$ to $1 \times 10^8$ cells (which may be administered at one to several doses), depending on the type of cancer, the stage of cancer progression, etc.

Hereinafter, the present invention will be described more specifically with reference to Examples. However, the technical scope of the present invention is not intended to be limited to these examples.

EXAMPLES

Example 1

Endothelial progenitor cells were separated and prepared from bone marrow as follows: mouse thigh bones or the like were disrupted using a mortar and DPBSE (PBS containing EDTA at a concentration of 5 mM) to collect a bone marrow fluid. From the collected bone marrow fluid, cells were collected according to a standard method. The obtained cells were filtered through a membrane filter of 70 µm in diameter, and the collected cells were suspended in 10 ml of DPBSE. This suspension was gently layered in a 15-ml centrifuge tube containing 4 ml of Histopaque 1083 (Sigma-Aldrich, Inc.). This mixture was used in density gradient centrifugation (400 g, 20 min., room temperature). Then, cells layered in between were collected using a pipette, and bone marrow mononuclear cells (BM-MNC) were isolated therefrom. The isolated cells were cultured for 4 days using a medium EGM-2-MV for microvascular endothelial cells (Clontech) on a plate coated with rat vitronectin (Sigma-Aldrich, Inc.) to obtain mouse endothelial progenitor cells as adherent cells. 95% or more of the adherent cells were confirmed to be cells of the endothelial system that exhibited uptake of DiI-labeled acetylated LDL and affinity for FITC-lectin (FIG. 1). These mouse endothelial progenitor cells were suspended in PBS (pH 7.4), and the cell suspension with each concentration of $1\times10^4$, $1\times10^5$, or $1\times10^6$ cells was subjected to subsequent experiments.

Example 2

Figure 2:
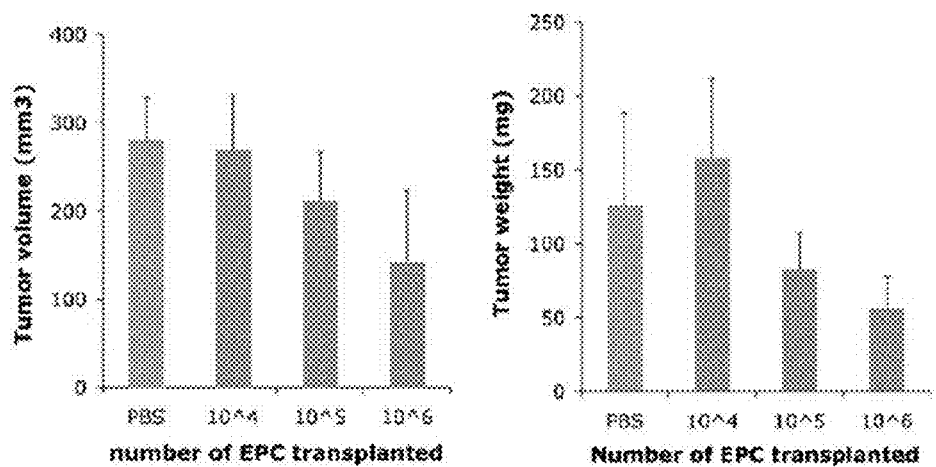
FIG. 2 is a diagram showing results of measuring tumor volumes (mm$^3$) and weights of cancer obtained by transvenously administering mouse endothelial progenitor cells in the range of $1 \times 10^4$ to $1 \times 10^6$ cells to cancer-bearing nude mice having a hypodermically transplanted human pancreatic cancer cell strain.

The mouse endothelial progenitor cells prepared in Example 1 were transvenously administered in the range of $1\times10^4$ to $1\times10^6$ cells to cancer-bearing nude mice having a hypodermically transplanted human pancreatic cancer cell strain KP-1N (JCRB0177.0). The results of measuring the tumor volumes (mm$^3$) and weights of pancreatic cancer for 2 to 4 weeks are shown in FIG. 2 for the individuals (n=10) that received the transplantation of the endothelial progenitor cells at each concentration. Individuals that received the transvenous administration of PBS in the same way as above were used as controls. In this context, the measurement of the tumor volumes (mm$^3$) of pancreatic cancer was performed according to a method described in the document (Mizukami Y, et al., Nat Med 11, 992-997, 2005). As a result, tumor growth inhibition was confirmed in the individuals that received the transplantation of $1\times10^5$ or more endothelial progenitor cells, in the 2- to 4-week observation period. Moreover, a human pancreatic cancer cell strain Panc-1 (ATCC No. CRL1469) or BxPC3 (ATCC No. CRL1687) was used in the same experiment as above, instead of the human pancreatic cancer cell strain KP-1N (JCRB0177.0). As a result, tumor growth inhibition as seen using KP-1N (JCRB0177.0) was also confirmed.

Example 3

Figure 3:
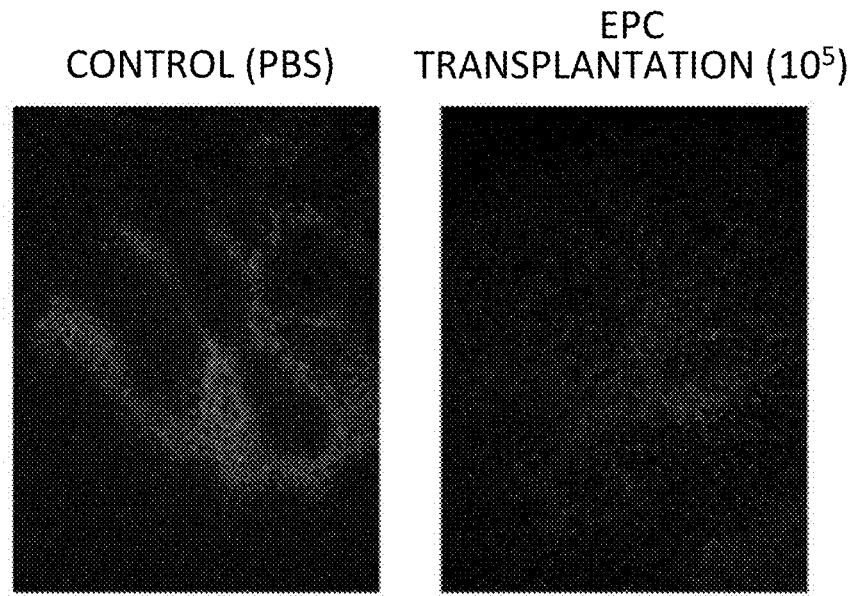
FIG. 3 is a diagram showing immunohistological staining results obtained by transvenously administering mouse endothelial progenitor cells at a dose of $1 \times 10^5$ cells to cancer-bearing nude mice having a hypodermically transplanted human pancreatic cancer cell strain and by transvenously administering PBS as a control.

The mouse endothelial progenitor cells were transvenously administered in the range of $1\times10^4$ to $1\times10^6$ cells to cancer-bearing nude mice having a hypodermically transplanted human pancreatic cancer cell strain KP-1N (JCRB0177.0). 90 minutes before slaughter, pimonidazole hydrochloride (Hypoxyprobe-1; Chemicon) generally used as a hypoxia marker was intraperitoneally administered at a dose of 60 mg/kg to the mice. The tumor was immunohistologically stained with anti-Hypoxyprobe-1 antibodies. The immunohistological staining results (n=10) are shown in FIG. 3, which were obtained by transvenously administering the mouse endothelial progenitor cells at a dose of $1\times10^5$ cells and by transvenously administering PBS as a control. A staining-positive region was evaluated as a low-oxygen region. Reduction of a hypoxic region(s) in the tumor was confirmed in the individuals that received the transplantation of $1\times10^5$ or more endothelial progenitor cells, in the 2- to 4-week observation period. Moreover, a human pancreatic cancer cell strain Panc-1 (ATCC No. CRL1469) or BxPC3 (ATCC No. CRL1687) was used in the same experiment as above, instead of the human pancreatic cancer cell strain KP-1N (JCRB0177.0). As a result, reduction of a hypoxic region(s) in the tumor as seen using KP-1N (JCRB0177.0) was also confirmed.

Example 4

Figure 4:
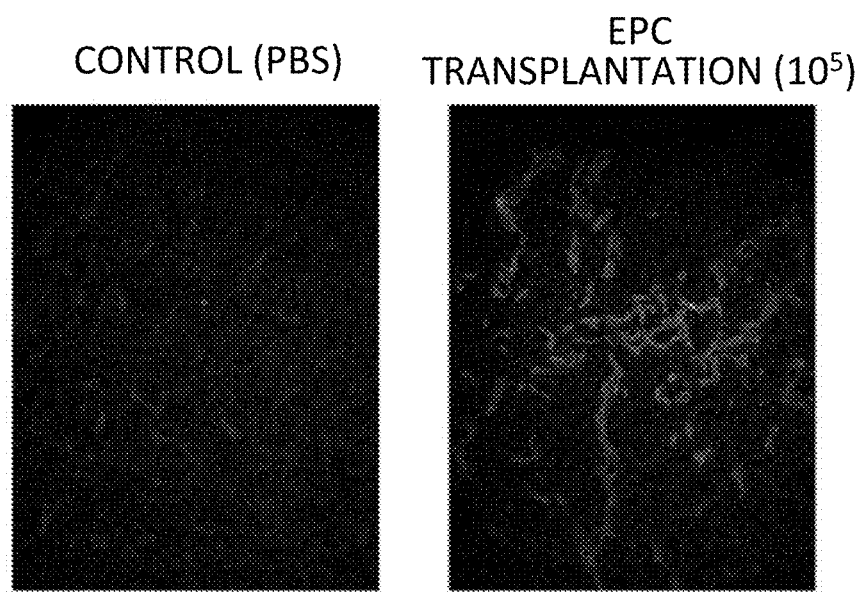
FIG. 4 is a diagram showing structural change in tumor vessel caused by transvenously administering mouse endothelial progenitor cells at a dose of $1 \times 10^5$ cells to cancer-bearing nude mice having a hypodermically transplanted human pancreatic cancer cell strain and by transvenously administering PBS as a control.

The mouse endothelial progenitor cells were transvenously administered in the range of $1\times10^4$ to $1\times10^6$ cells to cancer-bearing nude mice having a hypodermically transplanted human pancreatic cancer cell strain KP-1N (JCRB0177.0). 20 minutes before slaughter, 50 mg of FITC-labeled tomato lectin (Vector Laboratories, Inc.) was transvenously administered to the mice to label functional blood vessels. Structural change in tumor vessel (n=10) is shown in FIG. 4, which was caused by transvenously administering the mouse endothelial progenitor cells at a dose of $1\times10^5$ cells and by transvenously administering PBS as a control. As a result, structural change in tumor vessel (enlargement of vascular lumens) as well as an increase of blood flow caused thereby was confirmed in the individuals that received the transplantation of $1\times10^5$ or more endothelial progenitor cells, in the 2- to 4-week observation period. Moreover, a human pancreatic cancer cell strain Panc-1 (ATCC No. CRL1469) or BxPC3 (ATCC No. CRL1687) was used in the same experiment as above, instead of the human pancreatic cancer cell strain KP-1N (JCRB0177.0). As a result, structural change in tumor vessel (enlargement of vascular lumens) as well as an increase of blood flow caused thereby, as seen using KP-1N (JCRB0177.0), was also confirmed.

Example 5

To examine whether human endothelial progenitor cells could promote angiogenesis via paracrine secretion, HUVEC, the endothelial progenitor cells, and so on were cocultured on Matrigel for lumen (capillary) formation assay. The human endothelial progenitor cells used were endothelial progenitor cells derived from peripheral blood obtained from healthy volunteers. When a large amount of endothelial progenitor cells was required, samples obtained from apheresis for treatment of ulcerative colitis patients were used. Histopaque 1077 (Sigma-Aldrich, Inc.) was used in density gradient centrifugation (400 g, 20 min., room temperature). Then, cells layered in between were collected using a pipette, and mononuclear cells were isolated therefrom. The isolated cells were cultured for 4 to 7 days using EGM-2 complemented by a medium EGM-2-MV kit for microvascular endothelial cells (manufactured by Clontech, San Diego, Calif., USA) on a plate coated with human fibronectin to obtain human endothelial progenitor cells as adherent cells.

Figure 5:
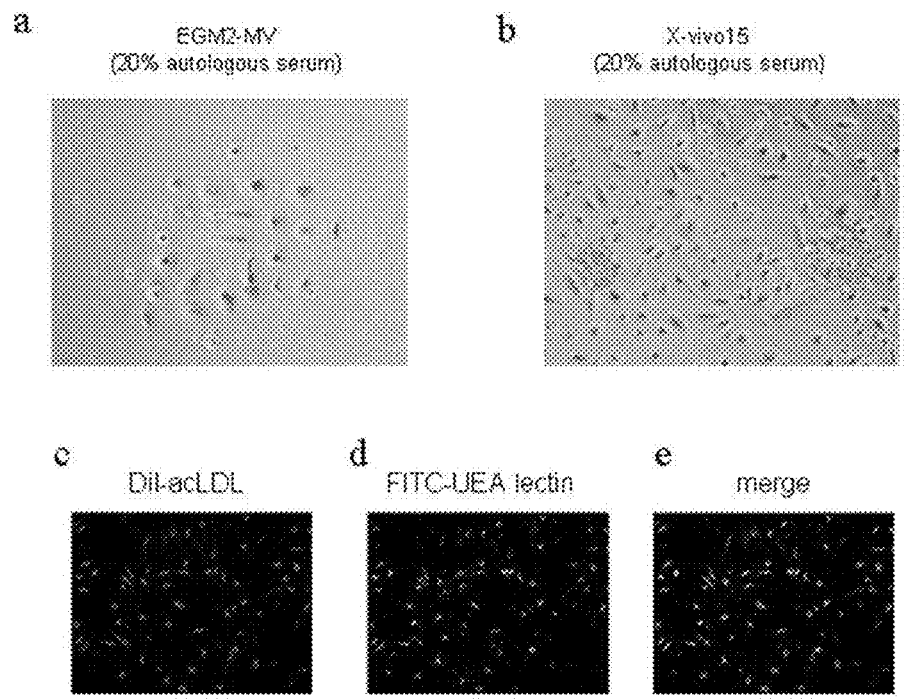
FIG. 5 is a diagram showing endothelial progenitor cells prepared from human peripheral blood mononuclear cells in EGM-2-MV (FIG. 5-a), and endothelial progenitor cells prepared therefrom in X-vivo 15 supplemented with VEGF, FGF, and autologous serum (FIG. 5-b). 95% or more of the endothelial progenitor cells prepared in EGM-2-MV were stained red, demonstrating DiI-acLDL uptake (FIG. 5-c). Moreover, 95% or more of the endothelial progenitor cells were stained green, demonstrating fluorescein isothiocyanate-Ulex lectin binding (FIG. 5-d). A diagram obtained by superimposing FIGS. 5-c and 5-d is also shown (FIG. 5-e)

Moreover, the human endothelial progenitor cells could also be obtained by inducing the differentiation of human peripheral blood mononuclear cells in a medium prepared by adding VEGF (vascular endothelial growth factor) (10 ng/mL), FGF (fibroblast growth factor) (10 ng/mL), and autologous serum (1 to 20%) to a culture solution of X-vivo 15 (manufactured by Lonza Group Ltd.) used in the culture of stem cells and monocyte-lineage cells. The endothelial progenitor cells are shown in FIG. 5-*a*, which were prepared by culturing human peripheral blood mononuclear cells for 2 weeks in a medium EGM-2-MV for microvascular endothelial cells supplemented with autologous serum (20%) instead of fetal bovine serum. The endothelial progenitor cells are shown in FIG. 5-*b*, which were prepared by culturing human peripheral blood mononuclear cells for 2 weeks in X-vivo 15 supplemented with VEGF, FGF, and autologous serum (20%). Spindle-shaped adherent cells were found in both the cases.

95% or more of the adherent cells were confirmed to be cells of the endothelial system that exhibited acetylated LDL (manufactured by Biomedical Technologies, Inc., Stoughton, Mass., USA) uptake activities (see FIG. 5-c) and were capable of binding to UEA (*Ulex europaeus* agglutinin) lectin (Vector Laboratories, Inc., Burlingame, Calif., USA) (see FIG. 5-d).

In the lumen assay, the human endothelial progenitor cells ($2.0 \times 10^3$ cells) labeled with DiI-acLDL were cultured using EGM-2 as a basal medium for endothelial cells and suspended in EBM-2 containing early-passage (passage 6 or earlier) HUVEC (human umbilical vein endothelial cell; 1000 cells) (manufactured by Cambrex Corp., Walkersville, Md., USA) and 2% FBS. The mixture was added to growth factor-free Matrigel (354230; manufactured by Becton Dickinson and Company, Franklin Lakes, N.J., USA) in a 96-well plate. The cells were cultured at 37° C. for 8 hours in the presence of 5% $CO_2$. The morphologies of the formed lumens were examined using a phase contrast-fluorescence microscope (IX70; manufactured by Olympus Corp.). The number of branch points per HPF (high power field) was measured, and the lumen length was quantified using Image J Software 1.38.

Figure 6:
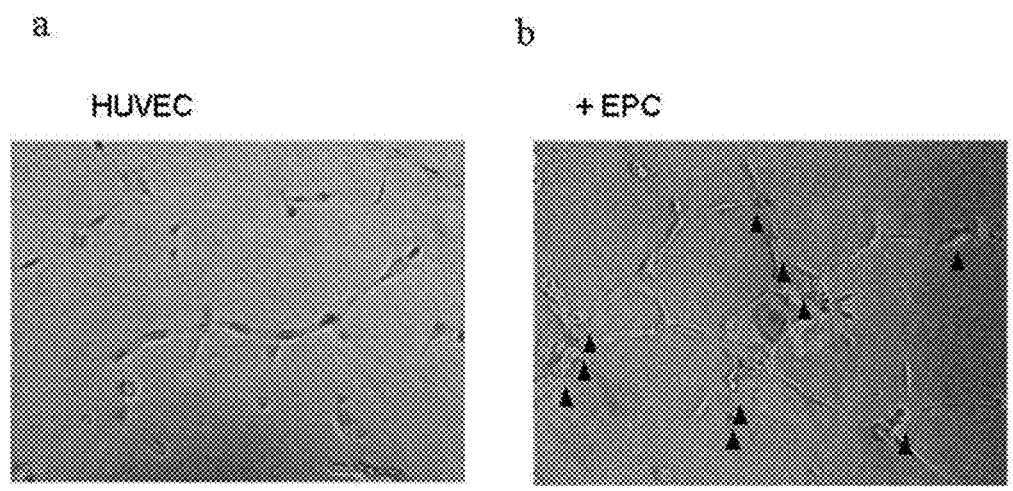
FIG. 6 is a diagram showing results of lumen formation assay. HUVEC (human umbilical vein endothelial cell) alone hardly formed a lumen structure (FIG. 6-a), whereas HUVEC cocultured with endothelial progenitor cells evidently induced capillary morphogenesis (FIG. 6-b)

HUVEC alone hardly formed a lumen structure under low-serum conditions (2% FBS in EBM-2) in the absence of growth factors such as VEGF (see FIG. 6-a). However, HUVEC cocultured with the human endothelial progenitor cells at a ratio of 5:1 evidently induced capillary morphogenesis (see FIG. 6-b). These results suggested that the adherent cells obtained by culturing human peripheral blood-derived mononuclear cells for 4 to 7 days using an EGM-2-MV medium on a plate coated with human fibronectin promote the lumen formation of endothelial cells such as HUVEC and have angiogenesis ability.

Example 6

Figure 7:
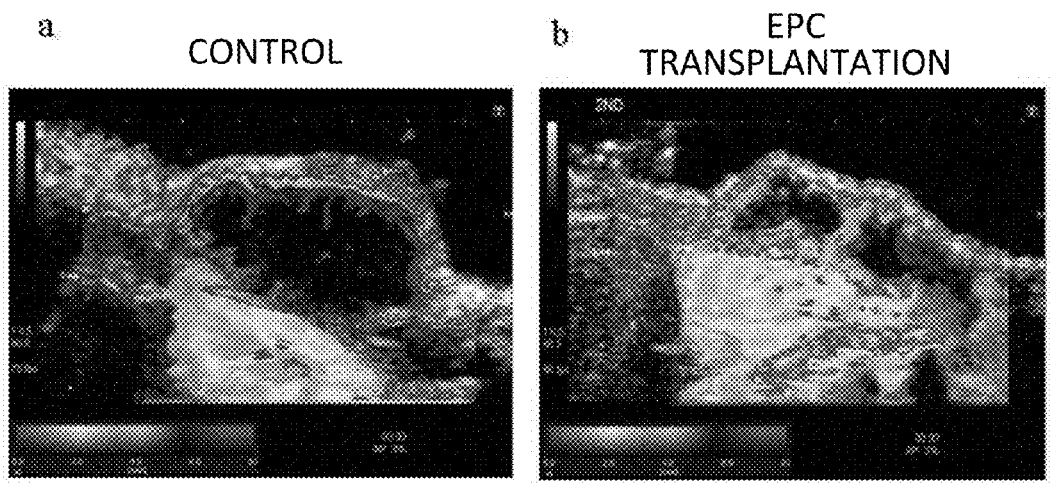
FIG. 7 is a diagram showing, using a bioimaging system, change in the area of blood flow distribution caused by transvenously administering mouse endothelial progenitor cells to cancer-bearing nude mice having a hypodermically transplanted human pancreatic cancer cell strain (FIG. 7-b) and by transvenously administering PBS as a control (FIG. 7-a)

The human endothelial progenitor cells obtained in Example 5 were transvenously administered to cancer-bearing nude mice having a hypodermically transplanted human pancreatic cancer cell strain KP-1N (JCRB0177.0). Immediately after transvenous injection of an ultrasonic contrast agent Sonazoid (registered trademark), the mice were photographed at a frequency of 8 to 14 MHz using a bioimaging system (Aplio XG; manufactured by Toshiba Medical Systems Corp.). The area of blood flow distribution is shown, which was obtained by transvenously administering the human endothelial progenitor cells at a dose of $5 \times 10^5$ cells a total of three times at two-day intervals (see FIG. 7-b) and by transvenously administering PBS as a control (see FIG. 7-a). As a result, enlargement of the area of blood flow distribution was confirmed in the individuals that received the transplantation of $5 \times 10^5$ human endothelial progenitor cells, in the 1- to 2-week observation period. These results are well consistent with the histological analysis results that showed enlargement of a microvascular density in tumor and reduction of a hypoxic region(s). Furthermore, the increase of blood perfusion in the tumor also strongly suggests the possibility leading to efficient drug distribution of anticancer agents or the like and effect enhancement for radiotherapy.

Example 7

Figure 8:
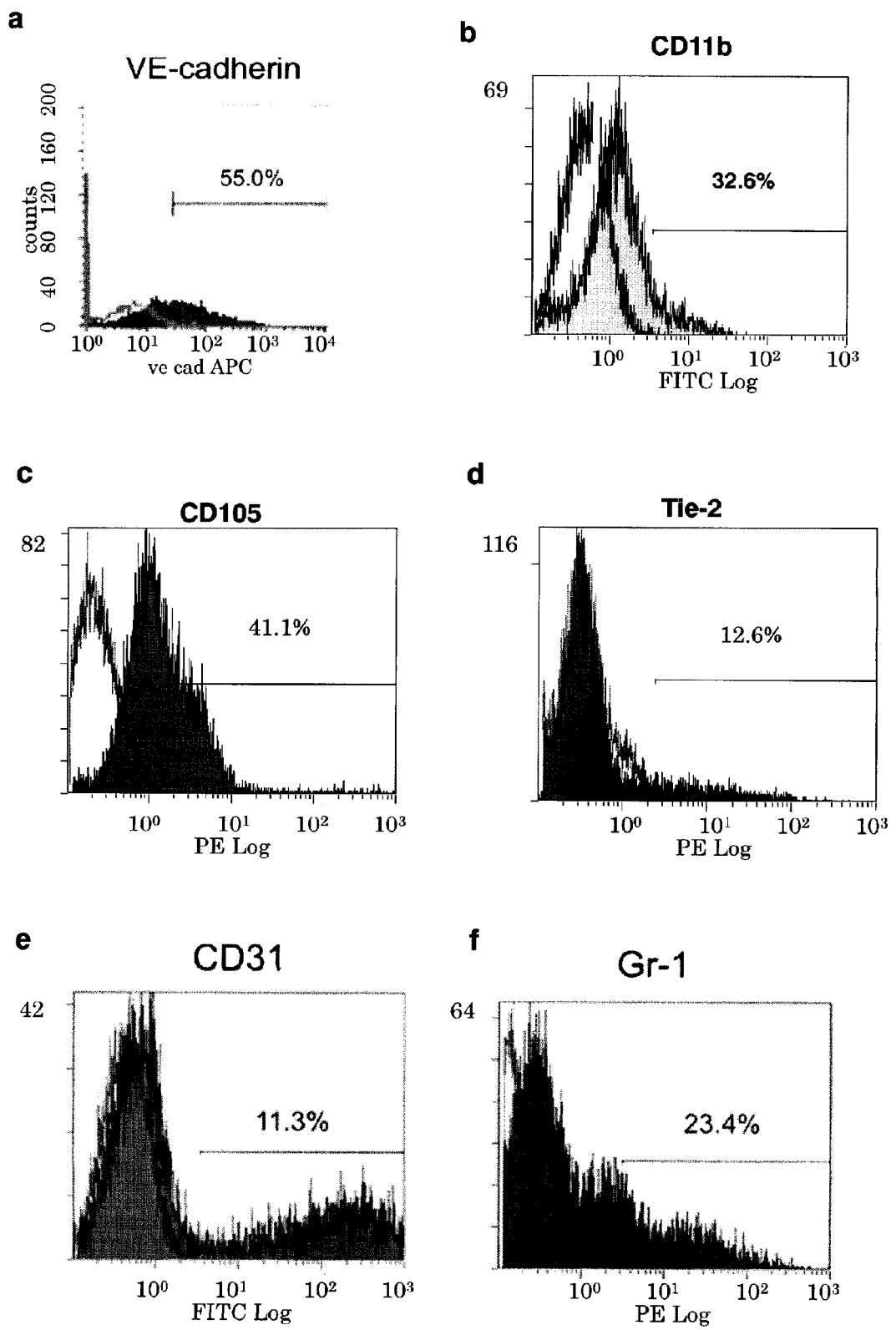
FIG. 8 is a diagram showing results of flow cytometry conducted on anti-mouse VE-cadherin antibodies (FIG. 8-a), anti-mouse CD11b antibodies (FIG. 8-b), anti-mouse CD105 antibodies (FIG. 8-c), anti-mouse Tie2 (CD202) antibodies (FIG. 8-d), anti-mouse CD31 antibodies (FIG. 8-e), and anti-mouse Gr-1 antibodies (FIG. 8-f)
Figure 9:
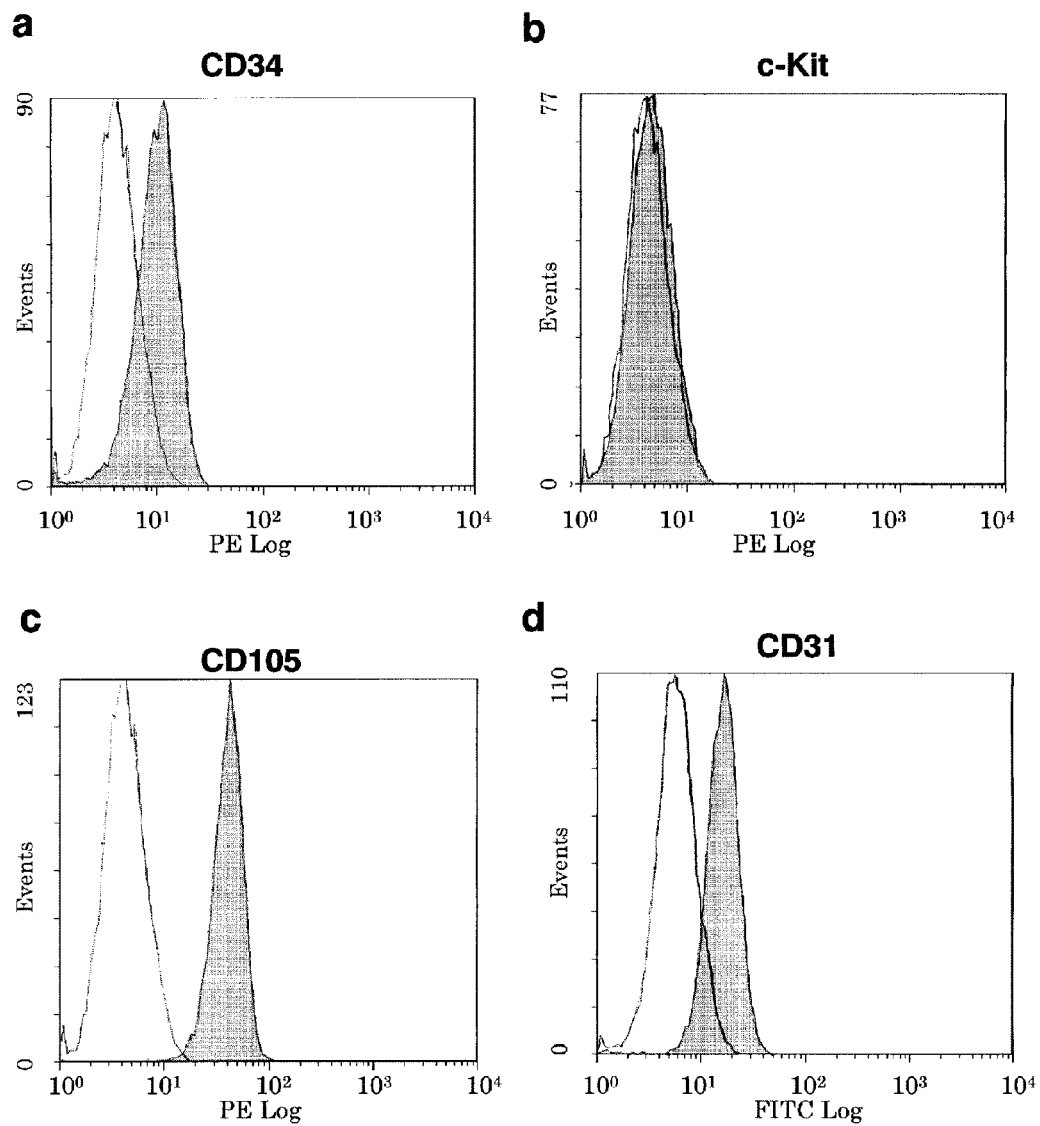
FIG. 9 is a diagram showing results of flow cytometry conducted on anti-human CD34 antibodies (FIG. 9-a), anti-human c-kit antibodies (FIG. 9-b), anti-human CD105 antibodies (FIG. 9-c), and anti-human CD31 antibodies (FIG. 9-d).

The properties of adherent cells were evaluated by flow cytometry. Adherent cells obtained by the method of Example 1 were left standing at room temperature for 30 minutes in a 60-mm to 100-mm temperature-sensitive culture dish (RepCell; manufactured by CellSeed Inc.) to prepare floating cells. This cell suspension was used as a sample in flow cytometry (manufactured by Beckman Coulter, Inc.) using anti-mouse VE-cadherin antibodies (manufactured by BD Biosciences Pharmingen), anti-mouse CD11b antibodies (manufactured by Beckman Coulter, Inc.), anti-mouse CD105 antibodies (manufactured by Beckman Coulter, Inc.), anti-mouse Tie2 antibodies (manufactured by R&D Systems, Inc.), anti-mouse CD31 antibodies (manufactured by Beckman Coulter, Inc.), and anti-mouse Gr-1 antibodies (manufactured by Beckman Coulter, Inc.) to confirm surface antigen expression in the adherent cells. The results are shown in FIG. 8.

A large number of cells positive to anti-mouse VE-cadherin antibodies (see FIG. 8-a), anti-mouse CD11b antibodies (see FIG. 8-b), mouse anti-CD105 antibodies (see FIG. 8-c), anti-mouse Tie2 (CD202) antibodies (see FIG. 8-d), anti-mouse CD31 antibodies (see FIG. 8-e), and anti-mouse Gr-1 antibodies (see FIG. 8-f) were observed in the adherent cells obtained by inducing the differentiation of mouse bone marrow mononuclear cells by culture.

The histological change in tumor (including blood vessel construction) and the tumor-reducing effect obtained by the transplantation of the cells obtained by inducing the differentiation of mouse bone marrow mononuclear cells in a medium for endothelial cells might be brought about by various cells (or cell groups) differing in the degree of differentiation or the expression pattern of the surface markers described above. Specifically, at this point, the functions of both cells were considered to be important, which were true progenitor cells that differentiate into endothelial cells as well as mononuclear cells (e.g., bone marrow-derived) that can promote the process in which endothelial cells construct and form neovascular vessels via cytokine production or the like.

Example 8

To examine the properties of adherent cells in the same way as in Example 7, the expression of a platelet-endothelial cell adhesion molecule (PECAM-1 (CD31)) and CD105 and the weak expression of CD34 were measured as general endothelial cell markers by the flow cytometry of adherent mononuclear cells. The adherent cells were positive to CD31 (55.7±7.7%), CD105 (90.4±3.1%), and CD34 (19.8±5.2%), but negative to c-kit (2.3±2.1%) (see FIGS. 9a to 9d).

Accordingly, the functions of both cells are probably important, which are true progenitor cells that differentiate into endothelial cells as well as mononuclear cells (e.g., bone marrow-derived) that can promote the process in which endothelial cells construct and form neovascular vessels via cytokine production or the like. Thus, blood circulation in tumor may be improved to the same level as that of normal tissues by transplanting, to cancer-bearing animals, the endothelial progenitor cells (EPC) in the narrow sense which are characterized by CD34 positive and VEGFR2 positive as well as various cells (or cell groups) including outgrow endothelial cells, vascular progenitor cells, vascular modulatory cells, Tie2-expressing monocytes, VEGFR1-positive myelomonocytic cells, CD11b-positive myelomonocytic cells, and the like, which are derived from mononuclear cells and have the ability to promote angiogenesis, as can be evident by Examples described above.

Industrial Applicability

According to the present invention, anticancer effects can be obtained by transplanting (transvenously administering) endothelial progenitor cells to an individual with cancer.

Thus, a novel cancer treatment system can be constructed. The endothelial progenitor cells can be obtained by inducing the differentiation of peripheral blood mononuclear cells. When autologous cells are used in the cell transplantation, safe treatment is achieved without the need of securing donors or without rejection. Moreover, during the course of the process in which tumor growth is inhibited by the transplantation of the endothelial progenitor cells, enlargement of tumor vessel caliber and improvement of blood flow are obtained, resulting in reduction of a hypoxic region(s) in the tumor. In such tumor, the drug distribution of anticancer agents or the like or the sensitivity of radiotherapy is enhanced. Thus, the transplantation of the endothelial progenitor cells can be expected to produce favorable anticancer effects. As described above, the transplantation of the endothelial progenitor cells can improve prognosis by withdrawing cancer tissues from a hypoxic state and controlling the malignant phenotypes of the cancer cells, such as invasive and metastatic capacity.

The invention claimed is:

1. A method for treating a tumor, comprising administering a composition consisting essentially of endothelial progenitor cells to a mammal, wherein the endothelial progenitor cells are adherent, are obtained from mammalian peripheral blood, bone marrow, or cord blood, and are capable of uptake of acetylated LDL and binding a lectin, and further wherein the endothelial progenitor cells have not been subjected to genetic engineering.

2. The method of claim 1, wherein the administered endothelial progenitor cells inhibit growth of the tumor.

3. The method of claim 1, wherein the administered endothelial progenitor cells reduce a hypoxic region(s) in the tumor.

4. The method of claim 1, wherein the administered endothelial progenitor cells induce remodeling of vessels of the tumor.

5. The method of claim 1, wherein the endothelial progenitor cells are administered transvenously.

6. The method of claim 1, wherein the tumor is selected from the group consisting of pancreatic cancer, esophagus cancer, gastric cancer, lung cancer, kidney cancer, thyroid cancer, parotid cancer, head and neck cancer, bone and soft tissue sarcoma, ureter cancer, bladder cancer, uterine cancer, liver cancer, breast cancer, ovarian cancer, and uterine tube cancer.

7. The method of claim 1, wherein the tumor is pancreatic cancer.

8. The method of claim 1 further comprising administering an anticancer agent(s) to the mammal, wherein activity of said anticancer agent(s) is enhanced by the administered endothelial progenitor cells.

9. The method of claim 1 which is combined with radiotherapy, wherein said radiotherapy has an effect that is enhanced by the administered endothelial progenitor cells.

10. The method of claim 1, wherein the lectin is FITC-lectin or *Ulex europaeus* agglutinin lectin.

* * * * *

UNITED STATES PATENT AND TRADEMARK OFFICE
CERTIFICATE OF CORRECTION

PATENT NO. : 8,491,887 B2  Page 1 of 1
APPLICATION NO. : 12/600530
DATED : July 23, 2013
INVENTOR(S) : Mizukami et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 617 days.

Signed and Sealed this
Eighth Day of September, 2015

Michelle K. Lee
*Director of the United States Patent and Trademark Office*